(12) United States Patent
Dal Moro et al.

(10) Patent No.: US 10,787,417 B2
(45) Date of Patent: Sep. 29, 2020

(54) PROCESS FOR THE PURIFICATION OF CAPROLACTAM FROM A SOLUTION OF CRUDE CAPROLACTAM WITHOUT ORGANIC SOLVENT EXTRACTION

(71) Applicant: AquafilSLO d.o.o., Ljubljana (SI)

(72) Inventors: Anacleto Dal Moro, Arco-Trento (IT); Michele Cecchetto, Arco-Trento (IT); Denis Jahic, Ljubljana-Smartno (SI); Vid Margon, Vrhnika (SI)

(73) Assignee: AquafilSLO d.o.o., Ljubljana (SI)

( * ) Notice: Subject to any disclaimer, the term of this patent is extended or adjusted under 35 U.S.C. 154(b) by 0 days.

(21) Appl. No.: 16/488,016

(22) PCT Filed: Dec. 15, 2017

(86) PCT No.: PCT/SI2017/050010
§ 371 (c)(1),
(2) Date: Aug. 22, 2019

(87) PCT Pub. No.: WO2019/117817
PCT Pub. Date: Jun. 20, 2019

(65) Prior Publication Data
US 2019/0382339 A1    Dec. 19, 2019

(51) Int. Cl.
| *C07D 201/16* | (2006.01) |
| *B01D 3/10* | (2006.01) |
| *B01D 3/14* | (2006.01) |
| *B01D 11/04* | (2006.01) |
| *C07D 201/06* | (2006.01) |
| *C07D 223/10* | (2006.01) |

(52) U.S. Cl.
CPC ............. *C07D 201/16* (2013.01); *B01D 3/10* (2013.01); *B01D 3/148* (2013.01); *B01D 11/0492* (2013.01); *C07D 201/06* (2013.01); *C07D 223/10* (2013.01)

(58) Field of Classification Search
CPC .................................................... C07D 201/16
See application file for complete search history.

(56) References Cited

U.S. PATENT DOCUMENTS 3,991,047 A    11/1976    Moudry et al.

FOREIGN PATENT DOCUMENTS

| GB | 1258810 A | 12/1971 |
| WO | 02070475 A1 | 9/2002 |

*Primary Examiner* — Bruck Kifle
(74) *Attorney, Agent, or Firm* — The Watson IP Group, PLC; Jovan N. Jovanovic (57) ABSTRACT

The present invention relates to a process for purifying caprolactam from solutions of crude caprolactam by a direct treatment with one or more alkaline compounds of polyvalent metals, preferably bivalent and trivalent, without resorting to organic solvent extraction as used in the usual purification process. A further subject of the present invention is a facility devoid of a unit for organic solvent extraction and designed to carry out the caprolactam purification process described herein.

14 Claims, 1 Drawing Sheet

PROCESS FOR THE PURIFICATION OF CAPROLACTAM FROM A SOLUTION OF CRUDE CAPROLACTAM WITHOUT ORGANIC SOLVENT EXTRACTION

The present invention relates to a process for the purification of caprolactam by means of a treatment with alkaline compounds of polyvalent, preferably bivalent and trivalent, metals, which does not require organic solvent double extraction, as is instead the case in the usual purification process.

Caprolactam is the lactam of 6-aminohexanoic acid (or aminocaproic acid). Its production and purification are of great relevance, since caprolactam is the monomer used in the production of polyamide 6, commonly known as Nylon 6.

Caprolactam is generally obtained by the reaction known as the "Beckmann rearrangement", by means of which cyclohexanone oxime is converted into caprolactam. Cyclohexanone oxime can be prepared by reacting cyclohexanone with hydroxylamine, the latter being obtained in turn by means of Raschig's process or by reducing nitrogen oxide with hydrogen. More recently, cyclohexanone oxime can also be prepared by means of ammoximation, by directly reacting cyclohexanone with ammonia and hydrogen peroxide without use of hydroxylamine. The Beckmann rearrangement is performed in the presence of oleum, which is a mixture of $SO_3$ and $H_2SO_4$. Caprolactam is therefore dissolved in a completely acidic medium, which is then neutralized using ammonia ($NH_3$): this neutralization leads to the formation of ammonium sulfate, which is separated by crystallization. After crystallization of the ammonium sulfate, the remaining aqueous solution contains approximately 70-80% by weight caprolactam relative to the total weight of the solution and a number of both inorganic byproducts (including residual ammonium sulfate) and organic byproducts of various nature, including linear or cyclic acids, lactones, or compounds of the amide, amine, ketone type, etc., with a more detailed description provided further below.

Hereinafter, the term "(solution of) crude caprolactam" shall mean an aqueous solution comprising approximately 70-80% by weight caprolactam relative to the total weight of the solution and organic and inorganic byproducts; the solutions of crude caprolactam are typically obtained at the end of the chemical synthesis processes for caprolactam (following neutralization with ammonia) or at the end of the processes for recovery of caprolactam (including processes of depolymerization of the polyamide 6 waste from industrial processes and/or depolymerization of the polymer itself at the end of its life cycle).

In general, the byproducts of caprolactam can be classified into substantially hydrophilic byproducts, substantially lipophilic byproducts, and byproducts having chemical characteristics similar to those of caprolactam itself.

The process currently generally used to purify crude caprolactam so as to obtain a monomer suitable for polymerization into Nylon 6 involves the following steps:

a) neutralizing the acidic byproducts with NaOH; since many byproducts are directly or indirectly acidic, the neutralization with NaOH makes it possible to form their respective sodium salts, which are soluble in water but not in the organic solvents used subsequently;

b) performing a first extraction with solvent, performed in a suitable extraction column provided with a suitable number of theoretical stages associated with an equilibrium of distribution of caprolactam between water and solvent; suitable solvents are benzene, toluene and trichloroethylene. The concentration of the caprolactam in the solvent is approximately 20% by weight using benzene, approximately 10% by weight using toluene. Trichloroethylene is currently being phased out due to problems associated with its environmental impact and toxicity. The solution of caprolactam in the solvent leaves at the head of the column, whereas an exhausted aqueous solution containing inorganic salts, organic compounds soluble in water and a residual amount of generally negligible caprolactam remains at the bottom. This solution containing salts and byproducts is discharged for appropriate disposal depending on the characteristics of the contaminants (COD, pH, etc.). The first extraction thus separates the byproducts of the hydrophilic type from caprolactam.

c) performing a second extraction with water: the caprolactam is re-extracted from the solvent with water in a second extraction column. In this extraction, the byproducts of the lipophilic type remain in the solvent, whereas the caprolactam passes into the aqueous phase. To obtain a good separation of the lipophilic byproducts from caprolactam, and taking into account the distribution coefficient between the two liquids, the concentration of caprolactam in the aqueous phase must be maintained at around 30% by weight, although caprolactam per se is completely soluble in the aqueous medium. In this case as well, the extraction column must therefore be provided with a suitable number of theoretical stages to guarantee the efficiency of the extraction of caprolactam from the solvent and to minimize loss thereof. The solution of caprolactam in water is recovered from the bottom of the second extraction column and fed to an apparatus for concentration thereof, generally an evaporator having multiple vacuum stages.

d) distilling the solvent: the solvent leaving the second extraction column, containing the lipophilic byproducts, is recycled and re-used in the first extraction; however, said solvent must itself be purified by distillation to guarantee a constant quality of the caprolactam. This solvent is therefore fed to a column having multiple plates for steam distillation. The low-boiling solvent is recovered at the head of the column and recirculated. For the purposes of the distillation, it should be borne in mind that both benzene and toluene, in vapor phase, form homogenous azeotropic mixtures with water, and it is possible to separate the two components only after condensation, thus complicating the recovery of the solvent itself from the viewpoint of the facility used. What remain at the bottom of the distillation column are substantially organic byproducts of the lipophilic type with a minimum quota (low, but not zero) of solvent: such distillation residue is fed to disposal by combustion/incineration;

e) extracting the caprolactam from the ammonium sulfate solution: after the neutralization with $NH_3$ of the acidic mixture of caprolactam in oleum, the ammonium sulfate solution to be fed to crystallization contains a percentage of caprolactam (from 2% to 4% by weight), which must be recovered. The solvent recovered from the distillation (step d)) is therefore initially fed to a third extraction column and contacted with the aqueous solution of ammonium sulfate. A diluted organic solution of caprolactam is thus recovered and, after this stage, the solvent is re-used in the first extraction described under point b);

f) concentrating the aqueous solution containing approximately 30% by weight caprolactam obtained from the second extraction: for this purpose, a three-stage concentrator is generally used in order to minimize steam consumption.

On the basis of that described above, it is clear that the successive extractions and concentrations necessary to obtain the purified product, which represent a fundamental aspect of the traditional process of purification of caprolactam, have a significant effect on the complexity both of the process and of the facility involved.

In fact, the process of traditional purification based on solvent double extraction requires a wide range of diverse equipment of complex and specific design, including: a reactor with agitator for neutralization with NaOH of the acidic impurities; two columns for recovery of caprolactam by means of solvent extraction; a column for recovery of caprolactam by means of water extraction; a multi-stage distillation column for purification of the solvent from the byproducts; decanters for separating the organic phase of the solvent from the aqueous phases; stores and vessels for the solvent used; a blanketing system for avoiding losses of solvent and the subsequent risks of flammability if the solvent comes into direct contact with air; a concentrator, generally having three stages, for concentrating the caprolactam; an elevated number of standard pieces of equipment (vessels, pumps, exchangers, etc.). The traditional process is therefore particularly complex from a technical viewpoint, and consequently the management of the operations is laborious and costly.

In addition, the traditional process has the disadvantage of using organic solvents in various steps, with negative consequences from environmental and safety viewpoints. Although, working with suitable facility and personal protective measures, it is possible to almost entirely eliminate the risks to individuals and the environment, there is still a need to consider the possibility that, in the event of an accident, potentially critical hazards might arise, associated with the presence of the solvents. As already mentioned, the solvents used in the traditional process for purification of caprolactam are benzene, toluene and trichloroethylene. Consequently, the following parameters related to hazards in respect of human and environmental safety in case of accidents and/or leaks have been reported for solvents of this kind:

cess can be more easily controlled and requires a reduced number of steps compared to the traditional process. In addition, a further objective of the present invention is to provide a facility for the purification of caprolactam by means of the process described herein, which facility requires a reduced range of equipment and is of simple construction and operation. A further objective of the invention is to provide a process and a facility for purifying caprolactam that can be provided relatively easily at a competitive cost.

BRIEF DESCRIPTION OF THE FIGURE

This object, as well as this and other objectives which will be explained in greater detail hereinafter and presented in FIG. 1 which shows block diagram of the process for the purification of caprolactam according to the invention.

DETAILED DESCRIPTION OF THE INVENTION

Figure 1:
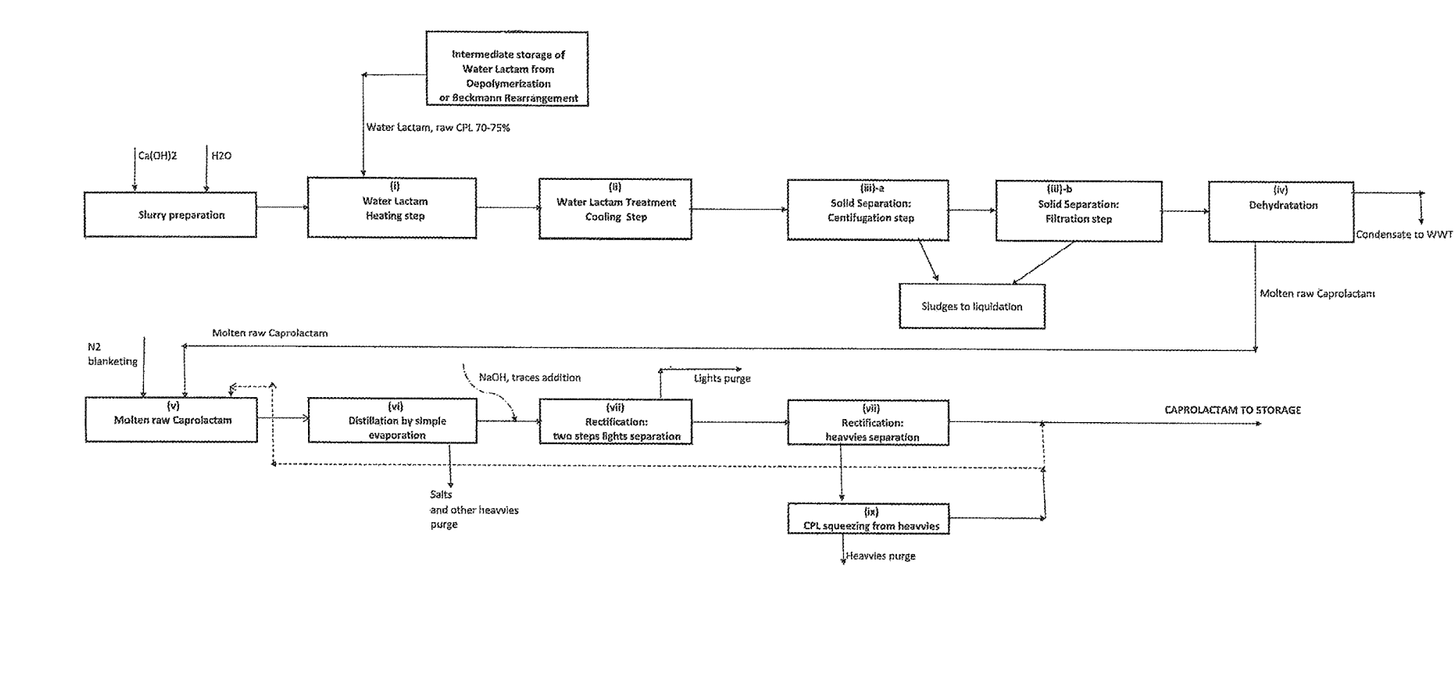

A process for the purification of caprolactam from a solution of crude caprolactam comprising the following steps:

(i) treating the solution of crude caprolactam by means of direct contact with one or more alkaline compounds of polyvalent metals, at a temperature between 50° C. and 110° C., for a duration of from 1 hour to 5 hours, under stirring, so as to thus obtain a suspension; wherein:

said one or more alkaline compounds of polyvalent metals are selected from the group formed of: bivalent alkaline earth metal hydroxides; bivalent alkaline earth metal oxides, bivalent alkaline earth metal carbonates; amphoteric polyvalent metal hydroxides having alkaline behavior when placed in contact with acids; amphoteric polyvalent metal oxides having alkaline behavior when placed in contact with acids; and mixtures thereof; and

|  | Benzene | Toluene | Trichloroethylene |
|---|---|---|---|
| Flash point | −11° C. (very flammable) | +4° C. (very flammable) | +73° C., thermally unstable |
| Explosive limits | 1.2-8.6% vol. | 1.1-7.1% vol. | 7.9-100% (12.5-90%) |
| $LD_{50}$, rat, oral administration | 930 mg/kg | 5000 mg/kg | 5400 mg/kg |
| TLV-TWA | 0.5 ppm | 50 ppm | 50 ppm |
| Risk phrases (of greater significance) | H340: can cause genetic modifications; H350: can cause cancer. | H373: can cause organ damage in case of prolonged or repeated exposure; H361: suspected to harm fertility or the fetus. | H350: can cause cancer; H341: suspected to cause genetic modifications; H412: harmful to aquatic organisms with long-term effects. |
| IARC category | Category 1: carcinoaenic to humans | — | Category 2A: probably carcinogenic to humans (*) |

(*) trichloroethylene was added by the EChA (European Chemicals Agency) to the list of classified SVHCs (substances of very high concern) as carcinogenic in June 2010 (ED/30/2010); the fixed limit in products for SVHCs must be less than 0.1%, and specific authorization is necessary for their use, with the objective of avoiding their use in the future.

It therefore appears clearly to be important to be able to provide an alternative method for improving the safety of the process in question in terms of human and environmental health.

The object of the present invention is therefore to provide a process for the purification of caprolactam which overcomes the drawbacks of the known processes used traditionally. Within the scope of this object, in particular, one objective of the invention is to provide a process for purifying caprolactam without resorting to the use of organic solvents. Another objective of the invention is to provide a more stable process for purifying caprolactam, which prosaid one or more alkaline compounds of polyvalent metals are present overall in an amount between 0.5% and 5% by weight relative to the total weight of the suspension;

(ii) cooling the suspension of step (i) and holding it at a temperature between 20° C. and 35° C., for a duration between 1 hour and 6 hours, under stirring, in order to maintain the homogeneity and stability of the suspension;

(iii) separating the solids from the suspension of step (ii) to obtain an aqueous solution of crude caprolactam.

Separation is preferably performed in two steps, i.e. making a first separation of most of the suspended solids by centrifugation (iii-a), followed by filtration (iii-b) of the residual fine solids in the suspension by means of a pressurized vessel equipped with filter cloths so as to obtain an aqueous solution of crude caprolactam.

Further features and advantages will become clear from the description provided hereinafter of a number of embodiments of the process according to the invention in preferred, but not exclusive conditions.

The process according to the present invention makes it possible to obtain purified caprolactam from solutions of crude caprolactam originating from processes for production thereof (in particular from solutions obtained by the Beckmann rearrangement, following separation of the ammonium sulfate) or from processes for recovery thereof (after depolymerization of Nylon 6 waste and residues).

The solutions of crude caprolactam typically contain approximately 70-80% by weight of caprolactam relative to the total weight of the solution and a series of hydrophilic byproducts, lipophilic byproducts, or byproducts having chemical characteristics similar to those of caprolactam itself, which must be removed in order to obtain the pure monomer, suitable for polymerization into Nylon 6. Although it is not possible to know and list all possible contaminants, the following can be cited as primary contaminants:

unsaturated organic byproducts, such as cyclohexanones (residue from the initial production of cyclohexanone oxime) and derivatives thereof, such as cyclohexenones, hydroxycyclohexanones and other compounds with double bonds conjugated to the carbonyl group;

carboxylic acids, such as acetic acid, valeric acid and the like, typically with a chain between 2 and 6 carbon atoms, also in the form with a hydroxyl group generally on the carbon opposite the carboxylic group, which is very frequently the case for acids with chains between 4 and 6 carbon atoms;

alcohols and phenol derivatives, including the phenol deriving from the production of cyclohexanone;

lactones derived from the above-mentioned hydroxy carboxylic acids, typically butyrolactone, valerolactone, caprolactone;

light amines with 3-6 carbon atoms (possible presence also of small amounts of aniline);

linear amides, for example valeramide;

lactams (or cyclic amides) with a chain different from that of caprolactam, such as butyrolactam, valerolactam, alkyl lactams (typically methyl lactams such as 6-methyl valerolactam (6-methyl-2 piperidone), and methyl caprolactams);

N-alkyl lactams, such as N-methyl caprolactam, N-methyl valerolactam or also, in small amount, the equivalent N-acetyl lactams;

adipimides (amides with two carbonyl groups bound to nitrogen);

octahydrophenazine: one of the most known and critical byproducts, which forms in almost all processes for production of caprolactam, even in pure form in a very limited amount;

organic sulfonate compounds, produced following use of oleum for conversion of the oxime into caprolactam;

ammonium sulfate not completely separated in the crystallization step and present in residual quantity;

cyclic and linear oligomers of caprolactam, mostly formed by a number of units between 2 and 6 or even more.

The process according to the invention is based on a reaction, under the conditions mentioned above and which will be described in greater detail hereinafter, between the solution of crude caprolactam and one or more alkaline compounds of polyvalent metals selected from the group formed of: bivalent alkaline earth metal hydroxides; bivalent alkaline earth metal oxides, bivalent alkaline earth metal carbonates; amphoteric polyvalent metal hydroxides having alkaline behavior when placed in contact with acids; amphoteric polyvalent metal oxides having alkaline behavior when placed in contact with acids; and mixtures thereof. It has in fact surprisingly been found that alkaline compounds of polyvalent metals of this kind on the one hand allow the formation of salts that are insoluble in water of some byproducts of caprolactam that precipitate and are separated by filtration; on the other hand said compounds make it possible to convert many of the remaining byproducts into compounds that are in turn insoluble (and can be separated by precipitation) or that have a volatility different from that of caprolactam, such that they can be separated in the steps of distillation, i.e. evaporation, and final rectification and can be eliminated with the purging of the fractions of the light byproducts and of the heavy byproducts. This has been demonstrated by gas chromatography analyses, which show the disappearance of the peaks relating to the majority of the byproducts initially present in the solutions of crude caprolactam: the disappearance of the peaks after the treatment with the alkaline compounds indicates that the byproducts are salified or nonetheless chemically converted. In addition, the above-mentioned alkaline compounds advantageously inhibit the formation of cyclic and linear oligomers of caprolactam, promoting the recovery of the pure monomeric form of caprolactam.

In a preferred embodiment of the process according to the invention, the one or more alkaline compounds of polyvalent metals can be selected from the group formed of: bivalent alkaline earth metal hydroxides; bivalent alkaline earth metal oxides; amphoteric polyvalent metal hydroxides having alkaline behavior when placed in contact with acids; amphoteric polyvalent metal oxides having alkaline behavior when placed in contact with acids; and mixtures thereof; advantageously, the use of hydroxides and oxides, unlike carbonates, is not associated with any development of carbon dioxide, which needs to be discharged from the equipment, and thus avoids emission of this polluting gas into the atmosphere.

In a more preferred embodiment, the polyvalent metal can be an alkaline earth metal selected from calcium and magnesium. In another preferred embodiment, the alkaline compound used can be (trivalent) aluminum hydroxide. With regard to the mixtures of multiple hydroxides/oxides, a mixture of calcium hydroxide and magnesium hydroxide can preferably be used.

It is also preferable to use polyvalent metals in the form of hydroxides, which, since they have a free OH group, are more "ready" to react with the organic byproducts in comparison with the respective oxides. The hydroxide that is used most preferably is calcium hydroxide, due to its wide availability and its tendency to form salts that are hardly soluble in aqueous medium. It is not necessary to perform pre-purifications of the oxides or hydroxides used in the process; the degree of purity obtained with normal industrial production is suitable for their use in the present process.

In order to facilitate handling, the oxides and hydroxides can also be used in the process in the form of a slurry, specifically a dispersion in water having a concentration of solids equal to approximately 30-40% by weight relative to the weight of the dispersion itself. Because the slurry is a liquid mixture, it can also be dosed by means of a pumping system, this being a solution that has proven to be advantageous above all for processes performed continuously. In the form of dispersion in water, the oxides are converted into the respective hydroxides. However, the hydroxides can also be used in solid form, being added using a suitable dosing system to the solution of crude caprolactam placed under stirring.

The alkaline compounds of polyvalent metals are used in an amount between 0.5% and 5% by weight relative to the total weight of the suspension obtained by adding the alkaline compound to the solution of crude caprolactam; preferably, the amount of alkaline compounds of polyvalent metals can be between 2.0% and 3.5% by weight relative to the total weight of the suspension. The specific amounts used, within the indicated ranges, can vary depending on the type and quantity of byproducts present in the solution of crude caprolactam.

The treatment with the alkaline compounds can be performed batchwise or continuously. In the description provided here, reference is made to a batchwise process, however, in the case of the continuous process, the procedure is entirely the same, except for the fact that the various steps are performed by means of systems with automatic flow rate control, temperature control, filtration control, etc.

In step (i) of the process, referred to hereinafter as the "hot (treatment) step", the 70-80% solution of crude caprolactam, which has an acidic pH (normally between 4.5 and 6.5), is loaded into a reactor, placed under stirring, and heated to a temperature between 50° C. and 110° C. The heating can be performed by known methods, for example by means of a pre-heater and/or hot water jacket and/or steam. The solution can preferably be heated to a temperature between 80° C. and 95° C. and even more preferably between 80° C. and 90° C. In parallel, one or more alkaline compounds (in solid form or in the form of a dispersion in water) is/are loaded into the reactor, dosed such that the total concentration thereof is between 0.5% and 5.0% by weight relative to the weight of the suspension obtained by adding said one or more alkaline compounds to the solution of crude caprolactam.

For example, in order to have a final suspension comprising 2.5% of calcium hydroxide, 1000 kg of 75% solution of crude caprolactam and 110 kg of a 30% suspension in water of $Ca(OH)_2$ can be used; such that the mixture comprises:

a) crude caprolactam: 750 kg (69.5% in weight/weight of the suspension)

b) $Ca(OH)_2$: 27 kg (2.5% in weight/weight of the suspension)

c) $H_2O$: 303 kg (28.0% in weight/weight of the suspension)

The final suspension is held at the preselected temperature in the range of 50-110° C., under constant stirring, for a duration between 1 hour and 5 hours, preferably between 2 hours and 3 hours to complete all chemical transformations involving many byproducts despite the reaction of salification of acid-base type itself, has very quick kinetics. Under stirring conditions, the suspension remains stable and homogenous, with a tendency to assume a color passing from yellowish, initially, to dark brown.

In this step of the process, a small amount of ammonia generally forms, above all due to the presence of ammonium sulfate among the byproducts, after the following reactions:

Since ammonia is a pungent and irritating compound, although it is produced in a very modest amount it is necessary to direct the vents of the equipment involved towards a device for washing the gases (scrubber) such that the ammonia is absorbed in water and the resultant ammoniacal aqueous solution can be directly fed for recovery and re-use in specific areas, for example in the crystallization of the ammonium sulfate.

The process according to the invention advantageously does not require any nitrogen blanketing of the equipment; in fact, since the process is performed in aqueous phase and at relatively low temperatures, the caprolactam fundamentally does not come into contact with the oxygen in the air. In addition, the aqueous medium and the relatively low temperatures do not produce flammable vapors: even when performing the step of hot treatment with temperatures greater than 100° C., a certain pressure is created in the equipment caused by the water vapor, which thus generates an inert atmosphere.

Next, at the end of the hot step, step (ii) of the process of the invention is performed, referred to hereinafter as the "cold (treatment) step". The suspension is transferred into a second reactor, also provided with an agitation system. The suspension is cooled to a temperature between 20° C. and 35° C., preferably between 25° C. and 30° C., implemented by known means, for example by means of intermediate exchanger and outer cold water jacket. The cooling allows precipitation of the salts derived from the reactions between the byproducts of caprolactam and the one or more alkaline compounds, minimizing the percentage of salts that remain in solution.

The residence times at 20-35° C. are between 1 hour and 6 hours, preferably between 2 hours and 30 minutes and 3 hours and 30 minutes; a further extension of the residence time at 20-40° C. with constant stirring can be advantageous, although not compulsory.

At the end of the cold treatment step, separation (iii) of the solids from the suspension is performed to obtain an aqueous solution of crude caprolactam. Firstly the separation of most of the suspended solids is performed by centrifugation, and secondly the filtration of the residual fine solids is performed by means of pressurized equipment equipped with filter cloths, such as filter presses (traditional or automated), pressurized disc filters, rotary filters, and filtration systems with centrifuges. The filters can preferably be of the type with automatic discharge of the solid treated over the filter cloths; however it is possible to also use filters of the manual type. The filtration can preferably be performed over filter cloths coated with a layer (what is known as a "precoat") of diatomaceous earth: the use of the precoat has the twofold advantage of extending the service life of the filter cloths, by limiting clogging, and improving the efficiency of filtration, by also treating particles of small size.

At the end of the separation (iii), the concentration of the caprolactam in the solution is still 70-80% by weight, however its purity has increased: in particular, the solution is devoid of solids in suspension, and is clear and transparent.

Whereas the solids retained on the filter cloths are disposed of, the solution is fed to final purification treatments in order to eliminate the remaining byproducts. The final purification involves the following further steps:

(iv) dehydrating the aqueous solution of caprolactam obtained from the separation in step (iii), working at a temperature below 100° C. and at a pressure between 35 mbar and 45 mbar: this step eliminates water from the solution, and the concentration of caprolactam passes from 70-85% by weight to approximately 99% by weight, thus obtaining an anhydrous crude caprolactam;

(v) collecting and maintaining the anhydrous crude caprolactam at 110-120° C. under inert atmosphere of nitrogen for 1.5-2.5 hours in a stirred reactor to complete the transformation of the residual organic salts;

(vi) evaporating the anhydrous crude caprolactam obtained in step (v): this step eliminates the residual salts of the polyvalent alkaline compounds used in the initial steps of the treatment that do not evaporate, i.e. separating the salified polyvalent alkaline compounds;

(vii) rectifying the caprolactam obtained in step (vi) by means of a vacuum fractional distillation column provided with a suitable number of theoretical stages obtained via structured packages: in this step the light byproducts, i.e. lights, are evaporated and are therefore purged and removed; the more effective purge of light byproducts is obtained in a two step columns working in series: first step is removing all light byproducts from the crude caprolactam, the second step is squeezing the residual caprolactam from the lights to increase the final yield;

(viii) rectifying the caprolactam obtained in step (vii) by means of a vacuum fractional distillation column provided with a suitable number of theoretical stages obtained via structured packages: in this step the final purified caprolactam is evaporated, thus separating it from the heavy byproducts, i.e. heavies, which remain at the bottom of the column;

(ix) squeezing the product, i.e. heavies, remaining at the bottom of the column at the end of step (viii) and rectifying the caprolactam thus obtained by means of a vacuum fractional distillation column provided with a suitable number of theoretical stages obtained via structured packages: in this step, a further amount of residual caprolactam is recovered, thus separating it from the heavy byproducts, which are then purged and removed.

The residual caprolactam recovered in step (ix), depending on the quality, can be mixed with the purified caprolactam obtained in step (viii) or can be sent back to step (vi) of evaporation, whereas the heavy byproducts are purged and removed. In one embodiment, if a discontinuous (batch) system is used, steps (vi), (vii), (viii) and (ix) can be performed consecutively in the same fractional distillation column. However, it is preferable to use a continuous system to perform the process, using columns specifically dedicated to each of the steps (vi), (vii), (viii) and (ix).

In the context of the present invention, and as is known to a person skilled in the art, the term "squeezing" means the action of recovering the greatest amount possible of useful product by "squeezing" the residual materials, which are then removed. In this case, squeezing makes it possible to recover further caprolactam by evaporation, and can be performed both in continuous mode and in discontinuous (batch) mode.

Advantageously, it is also possible and convenient to perform the squeezing of the caprolactam also from the residual material obtained from the evaporation in step (vi) insofar as this contains, besides the salts of the alkaline compounds of polyvalent metals, up to 50-60% by weight of residual caprolactam. Squeezing is facilitated by the fact it has been found that the salts of the alkaline compounds of polyvalent metals used in the process according to the invention, in contrast to the salts of compounds of monovalent metals (for example of sodium or potassium), behave as inhibitors in processes of oligomerization/polymerization, as a result of which the evaporation residues remain in the molten state, both in high-vacuum conditions (10-15 mbar) and at atmospheric pressure, already at temperatures between 130° C. and 150° C., which are temperatures much lower than the melting point of Nylon 6 and of the cyclic and linear oligomers thereof. The successive distillation can therefore be performed in columns with recycling at the bottom and at temperatures between 130° C. and 150° C., thus avoiding the use of "falling film" evaporator apparatuses, such as those of the Luwa type.

As an alternative to direct squeezing, the residual materials from the evaporation, i.e. from step (vi) can be fed to one of the steps of neutralization of crude caprolactam output from the production reaction, for example in the stage of neutralization by recovery of ammonium sulfate. In this case, small amounts of sulfate of the metal used (for example calcium sulfate, magnesium sulfate, aluminum sulfate) will be found in the crystallized ammonium sulfate, which are nonetheless compatible with the use as a fertilizer of ammonium sulfate itself, or are potentially also useful as an anticaking agent.

Furthermore, in addition to steps (iv)-(ix) of final purification described above, one or more further purification treatments known to a person skilled in the art can also be performed, such as hydrogenation (for example with Raney nickel catalyst), passing through activated carbon, treatment with potassium permanganate ($KMnO_4$), treatment with ozone, etc.

Among the other, one of the most simple and useful treatments to improve the final quality of purified caprolactam, i.e. parameters like Permanganate Index PI, Absorbance at 290 nm, is mixing the anhydrous caprolactam from step (vi) with traces of NaOH in the amount of 0.05-0.5 by weight relative to anhydrous caprolactam and then submitting said mixture to the rectification/distillation steps as described above.

In another aspect, the invention relates to a section of the facility for purification of caprolactam in accordance with the process described here, comprising (a) a first reactor, in which the "hot" treatment of the solution of crude caprolactam is performed by addition of alkaline compounds of polyvalent metals (step (i) of the process). This first reactor is equipped with an agitator and, typically, with an outer jacket to allow heating, and is made of conventional stainless steel (AISI 304, AISI 316 and the like);

(b) a second reactor, in which the "cold" treatment of the suspension of crude caprolactam and alkaline compounds is performed (step (ii) of the process). This second reactor is also provided typically with an agitator and with an outer jacket to allow cooling, and is made of conventional stainless steel (AISI 304, AISI 316 and the like);

(c) a separation station comprising centrifuge and one or more pressurized filters equipped with filter cloths, in which step (iii) of the process is performed.

This section of the facility is a substitute of the section used for solvent extraction in traditional facilities.

The final filtration station can preferably be present in duplicate, such that there is always an operative line and a line in which solids are being discharged. The pressurized vessels equipped with filter cloths can be, for example, filter presses (traditional or automated), pressurized disc filters, rotary filters, or filtration systems with centrifuges. In addition, the filters used can preferably be of the type with automatic discharge of the solid retained by the filter cloths.

In addition, in one embodiment, the facility according to the invention also comprises the following equipment for final purification of the caprolactam, at the end of the treatment with the alkaline compounds:

(d) a column for dehydrating the filtered caprolactam solution, removing the water therefrom;

(e) an evaporation station for removing the salts of the alkaline compounds by evaporating the caprolactam;

(f) a distillation station, comprising a column for vacuum fractional distillation, equipped with structured packages, for separating the caprolactam from the light byproducts preferably in two steps and a column for vacuum fractional distillation, equipped with structured packages, for separating the caprolactam from the heavy byproducts.

In one embodiment of the facility, the evaporation station (e) can comprise one or more thin-film evaporators of the Luwa type, which are known and commonly used within the sector.

In another embodiment of the facility, the fractional distillation columns used in step (f) can be made of stainless steel, preferably of the AISI 304 or AISI 316 type. The structured packages present within the column can be made of stainless steel, preferably selected from those of the SULZER BX type and the like, Pall rings and Raschig mini-rings: packages of this type make it possible, in fact, to obtain an elevated number of theoretical plates per meter.

The columns for fractional distillation work also in high-vacuum conditions (specifically also at pressures less than 10 mbar, preferably between 3 and 10 mbar) and at column bottom temperatures up to 160° C.: these conditions make it possible to avoid the degradation of the distillation products. In addition, the columns for fractional distillation can work advantageously under reflux conditions, the extent of which is calculated and selected depending on the separation of the byproducts present.

At the head of each column there is a vapor condenser: the condenser at the head of the column (d) for dehydrating the solution typically uses mains water as cooling fluid at a temperature between 12° C. and 14° C., whilst the cooling at the head of the column for distillation of the caprolactam is typically performed using thermostatically controlled water at a temperature between 70° C. and 80° C., for the purpose of avoiding solidification of the caprolactam itself, the melting point of which is 69° C.

The facility according to the invention of course also comprises a series of standard items of equipment, the presence of which is immediately evident to a person skilled in the art, such as storage vessels, pumps, heat exchangers, valves, temperature and pressure measurement instruments, etc.).

It should be understood that the technical features of the embodiments described with reference to the process according to the invention are also to be considered as valid, where applicable, with reference to the corresponding apparatuses of the facility, and vice versa, even if not explicitly mentioned.

In the light of the description provided here, it has been found in practice that the process for purifying caprolactam by means of treatment with alkaline compounds of polyvalent metals according to the present invention fully achieves the object as presented above. In particular, the process according to the invention achieves the desired results, making it possible to obtain purified caprolactam, with significant advantages from a technical, safety, environmental and economical viewpoint compared to the traditional process of purification by means of solvent double extraction.

Firstly, from a technical and facility design viewpoint, the process according to the invention requires a more limited and simpler set of equipment compared to that used in the traditional process, as is clear from the above-provided description of the facility.

From an environmental and safety viewpoint, the process of the invention uses exclusively water as solvent and the alkaline solvents cited above as reagents. All of the compounds used are widespread and commonly used often also in common civilian day-to-day activities. Although compounds such as calcium hydroxide and oxide irritate the skin and the eyes, the personal protection of the operators is nevertheless very simple, involving gloves, goggles and anti-dust masks. The environmental impact of these compounds can be considered to be almost zero insofar as they are already present in nature in inorganic minerals and compounds.

Lastly, the process according to the invention is also economically advantageous compared to the traditional process by means of solvent double extraction, from two aspects. Firstly, it requires less capital outlay, thanks to the smaller amount and simpler design of the necessary equipment. Secondly, because the working sequence is simpler, the operating costs, maintenance costs, and above all the costs associated with material consumption, with particular reference to steam and electrical energy, are also lower. In addition, the costs of the alkaline compounds used are also very modest.

The process, conceived as described here, can be subject to numerous modifications and variants not departing from the scope of the inventive concept; in addition, all the details can be substituted by other elements which are known to be equivalents by a person skilled in the art.

The features of the process for purification of caprolactam according to the invention and the advantages thereof will now be demonstrated further on the basis of a few examples so as to enable improved comprehension of the process itself. These examples are not to be considered limiting in terms of the type and amount of compounds used, operational parameter ranges, etc.

EXAMPLES

In the tables presented in the examples, the following abbreviations correspond to the meanings below:
CPL=caprolactam;
GC=gas chromatography;
CPL refract=concentration of caprolactam in aqueous solution, determined by refractometry;
$H_2O$ KF=content of $H_2O$ in the solution, determined using the Karl-Fischer analysis method; In the tables, the The term "HAS Raschig process" refers to the process in which the hydroxylamine sulfate (HAS) used for the preparation of the cyclohexanone oxime was obtained with an elevated amount of sulfuric acid, which leads to the final co-production of approximately 4.5 kg of ammonium sulfate per 1 kg of caprolactam.

The concentration of the hydroxide is therefore equivalent to 2.5% by weight. The suspension, under continuous stirring, was brought to 50° C. by means of water at 95° C. fed into the outer jacket of the reactor and maintained under these conditions continuously for 2 hours. The flow of heating water was then shut off, and cooling with water at 25-30° C. was performed, keeping the stirring constant. The suspension was held at this temperature for 2 hours and 30 minutes, then it was discharged into a tank and subjected to filtration over a filter cloth. After the filtration, a dark yellow, but clear solution was obtained, with no solids in suspension.

The analytical data of the initial, untreated solution and of the treated solution are as follows:

| Sample | CPL refract [%] | $H_2O$ KF [%] | pH | Acidity or alkalinity [meq/kg] | Consumption of $KMnO_4$ [mg/kg solut.] | Ashes [%] | GC purity CPL [% area] | GC n° peaks |
|---|---|---|---|---|---|---|---|---|
| Initial solution | 72.1 | 28.0 | 5.9 | 9.4 (acidity) | 1185 | 0.0 | 99.7 | 9 + 1 (CPL) |
| Treated solution | 73.4 | 26.0 | 11.4 | 82.34 (alkalinity) | 1185 | 0.260 | 99.8 | 5 + 1 (CPL) | sum of CPL refract and $H_2O$ KF is close to, but not exactly equal to 100%, given the intrinsic error of these analyses, which are nevertheless useful in providing an indication of the progress of the process and can be performed very quickly.

The consumption of permanganate ($KMnO_4$) is an indicator of the amount of oxidizable substances that are present in the solution of crude caprolactam; it is not a specific quality parameter, but an indicator of the amount of present impurities sensitive to the oxidizing agents.

The gas-chromatography analysis was performed by dissolving the sample in methanol using a capillary column with stationary phase of the "crossbond-PEG" type (or also other type like Stabilwax Cap column) with predetermined temperature scanning: in addition to verifying the purity (in terms of area) of the peak corresponding to caprolactam, this analysis is used to verify which impurities remain following the treatment. Although not all the byproducts can be identified or quantified directly, this method makes it possible to perform a valid comparison of the effects of the treatment.

Example 1

Treatment with $Ca(OH)_2$

The following were introduced into a pilot reactor made of AISI 316 steel with a volumetric capacity of at least 100 liters, provided with an agitator and outer jacket:
solution of crude caprolactam with 72-73% by weight caprolactam from a "HAS Raschig" process: 45.00 kg;
anhydrous solid $Ca(OH)_2$: 1.15 kg.

In this case the HPLC analysis, performed in a column of the Zorbax Eclipse XDB-C18 type, revealed that no oligomers of caprolactam could be found in the treated solution, neither cyclic nor linear oligomers, demonstrating that the treatment according to the invention creates conditions that inhibit the pre-polymerization forms of caprolactam.

The analytical data reveal that the treatment fundamentally modifies the initial solution with the following primary effects:

1) the acidic solution becomes alkaline, which is an indispensable condition for the subsequent phases of distillation insofar as the highly acidic caprolactam never reaches the typical parameters of the commercial specifications;

2) the number of byproducts evidenced by way of gas chromatography is significantly reduced, which signifies that they have been transformed, salified and separated during the filtration phase.

The inspection of the effects of the treatment is indispensable in order to track and monitor the process, whereas the quality of the final caprolactam is verified by the distillation and rectification tests described further below.

Example 2

Treatment with $Ca(OH)_2$

The same amounts of caprolactam solution and of $Ca(OH)_2$ (45.00 kg of solution of crude caprolactam with 72-73% by weight of caprolactam from a HAS Raschig process and 1.15 kg of anhydrous solid $Ca(OH)_2$) were introduced into the same reactor from Example 1 under application of the same conditions. The concentration of the hydroxide was thus equivalent to 2.5% by weight. The temperature of the treatment in the hot phase was maintained at 85° C.

The analytical data of the initial, untreated solution and of the treated solution are as follows:

| Sample | CPL refract [%] | $H_2O$ KF [%] | pH | Acidity or alkalinity [meq/kg] | Consumption of $KMnO_4$ [mg/kg solut.] | Ashes [%] | GC purity CPL [% area] | GC n° peaks |
|---|---|---|---|---|---|---|---|---|
| Initial solution | 72.1 | 28.0 | 5.9 | 9.4 (acidity) | 1185 | 0.0 | 99.7 | 9 + 1 (CPL) |
| Treated solution | 80.8 (evap(*)) | 19.0 | 11.34 | 60.84 (alkalinity) | 1580 | 0.263 | 99.9 | 3 + 1 (CPL) |

(*)the rise in the refractometry concentration of caprolactam and the decrease in the content of $H_2O$ revealed by the analyses indicate that there was a loss of some water by evaporation, which in no way influences the treatment of the byproducts.

In this case the lower final alkalinity, with the same amount of $Ca(OH)_2$ used, can indicate a greater reactivity of the mixture, which is consistent with the fact that the gas chromatography demonstrates a further reduction of the number of byproducts. The behavior and conditions most suitable for the proposed treatment and the results obtained at this stage are dependent in each case on the effective composition of the starting solution of crude caprolactam, but remain within the ranges described in the text.

Example 3

Treatment with $Ca(OH)_2$

The following were introduced into the same reactor from Example 1 and under application of the same conditions:

solution of crude caprolactam with 73-74% by weight of caprolactam from a "HAS from NO reduction process": 45.00 kg;

anhydrous solid $Ca(OH)_2$: 1.15 kg-1.65 kg.

The "HAS from NO reduction" process means a process of preparing caprolactam via hydroxylamine sulfate (HAS) obtained by reduction of nitrogen oxide (NO) with hydrogen, which makes it possible to reduce the final co-production of ammonium sulfate to 2.2 kg per 1 kg of caprolactam.

The concentration of the hydroxide is thus equivalent to 2.5% and 3.5% by weight, respectively. The operating temperature was held at 85° C.

The analytical data of the initial, untreated solution and of the solutions after treatment are as follows:

It is noted that the solution of crude caprolactam obtained by means of a process different from the traditional "Raschig process" (but equally widespread however, or more widespread) also presents characteristics similar to those obtained in the examples above.

Example 4

Treatment with $Ca(OH)_2$

The following were introduced into the same reactor from Example 1 under application of the same conditions:

solution of crude caprolactam with 82-84% by weight of caprolactam from a recovery process: 45.00 kg;

anhydrous solid $Ca(OH)_2$: 1.15 kg.

The crude caprolactam used in this example originates from a recovery process, and therefore in itself is contaminated to a greater extent by impurities. It is noted that the percentage by weight of caprolactam, which is greater compared to the examples above, is dependent on the use of a smaller amount of water in the recovery process compared to the synthesis process.

The concentration of the hydroxide is thus equivalent to 2.5% by weight. The operating temperature was held at 80° C. for 2 hours, then the temperature was reduced to 25-30° C. for 2 hours and 30 minutes.

The analytical data of the initial, untreated solution and of the solution after treatment are as follows:

| Sample | CPL refract [%] | $H_2O$ KF [%] | pH | Acidity or alkalinity [meq/kg] | Consumption of $KMnO_4$ [mg/kg solut.] | Ashes [%] | GC purity CPL [% area] | GC n° peaks |
|---|---|---|---|---|---|---|---|---|
| Initial solution | 74.41 | 25.3 | 5.73 | 27.67 (acidity) | 1285 | 0.0 | 99.69 | 8 + 1 (CPL) |
| Solution treated with 2.5% $Ca(OH)_2$ | 82.18 (evap) | 17.60 | 11.90 | 96.1 (alkalinity) | 1216 | 0.381 | 99.85 | 6 + 1 (CPL) |
| Solution treated with 3.5% $Ca(OH)_2$ | 82.65 (evap) | 17.40 | 11.85 | 90.4 (alkalinity) | 1200 | 0.43 | 99.91 | 5 + 1 (CPL) |

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Initial solution | 84.1 | 15.10 | 4.20 | 74.6 (acidity) | n.a. | 0.33 | 88.9 | 24 + 1 (CPL) |
| Treated solution | 84.8 | 15.40 | 10.40 | 56.1 (alkalinity) | n.a. | 0.59 | 96.8 | 14 + 1 (CPL) |

It is noted that the solution of crude caprolactam obtained by means of a recovery process, and therefore having a greater concentration of byproducts, after the treatment according to the present invention also presents characteristics rather similar to those obtained in the examples above.

Example 5

Treatment with Ca(OH)$_2$

Proceeding from a single batch of crude caprolactam originating from a recovery process, and therefore particularly rich in byproducts and having an elevated initial acidity value, the following were introduced into the same reactor from Example 1 under application of the same conditions:
solution of crude caprolactam with 70-75% by weight of caprolactam from a recovery process: 45.00 kg;
anhydrous solid Ca(OH)$_2$: 1.15 kg.

The concentration of the hydroxide is thus equivalent to 2.5% by weight. Two different processes were performed: one at 80° C. and one at 95° C. for 2 hours and 30 minutes. The cooling at 25-30° C. was kept the same for both processes.

The analytical data of the initial, untreated solution and of solution after treatment are as follows:

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Initial solution | 70.6 | 29.79 | 4.50 | 141.7 (acidity) | n.a. | 0.14 | 86.20 | 38 + 1 (CPL) |
| Solution treated at 80° C. | 71.26 | 30.3 | 11.1 | 181 (alkalinity) | n.a. | 1.25 | 97.67 | 26 + 1 (CPL) |
| Solution treated at 95° C. | 71.12 | 30.75 | 11.2 | 202 (alkalinity) | n.a. | 1.24 | 96.10 | 21 + 1 (CPL) |

In this case as well it is noted that the solution of crude caprolactam obtained by means of a recovery process and particularly rich in byproducts, after the treatment according to the present invention also presents characteristics rather similar to those obtained in the examples above. It was also observed that some byproducts are completely eliminated, and therefore the number of byproducts reduces, whereas the amount of other byproducts is significantly reduced.

Example 6

Treatment with Ca(OH)$_2$

The following were introduced into a pilot reactor made of AISI 316 steel, having a volumetric capacity of 3000 liters and provided with an agitator and outer jacket:
solution of crude caprolactam with 75-80% by weight of caprolactam from a recovery process: 2500.00 kg;
anhydrous solid Ca(OH)$_2$ (amounts used in successive tests): 37.5 kg-50.0 kg-62.0 kg-75.0 kg-87.5 kg.

The concentration of the hydroxide in the solution of crude caprolactam is thus, in the various experimental tests, equivalent to: 1.5%; 2.0%; 2.5%; 3.0%; 3.5% by weight, respectively.

The suspension, under continuous stirring, was brought to a temperature of 85° C. by means of low-pressure steam fed into the outer jacket of the reactor and maintained under these conditions for 2-3 hours. The flow of heating water was then shut off, and cooling with water at 25-30° C. was performed, keeping the stirring constant. The suspension was held at this temperature for 3 hours, then it was subjected to filtration over a filter press with filter cloths made of low-permeability polypropylene. With each filtration, the preparation of a coating of diatomaceous earth was continued by means of the conventional procedure known for operations of this kind. After the filtration, a dark yellow, but clear solution was obtained, with no solids in suspension.

The analytical data of the initial, untreated solution and of the treated solutions are as follows:

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Initial solution | 76.0 | 21.20 | 4.0 | 215.8 (acidity) | 3350 | n.a. | 82.8 | — |

-continued

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Solution treated with 1.5% Ca(OH)$_2$ | 75.1 | 25.9 | 9.9 | 142.0 (alkalinity) | 3318 | n.a. | 93.1 | — |
| Initial solution | 76.3 | 21.9 | 3.8 | 232.8 (acidity) | 3334 | n.a. | 86.7 | — |
| Solution treated with 2% Ca(OH)$_2$ | 77.9 | 23.6 | 10.4 | 230.6 (alkalinity) | 3397 | n.a. | 96.66 | — |
| Initial solution | 83.5 | 15.7 | 4.6 | 197.1 (acidity) | 2844 | n.a. | 87.7 | — |
| Solution treated with 2.5% Ca(OH)$_2$ | 83.5 | 16.5 | 10.9 | 117.6 (alkalinity) | 2812 | n.a. | 98.0 | — |
| Initial solution | 79.2 | 19.4 | 4.5 | 217.6 (acidity) | 2686 | n.a. | 81.32 | — |
| Solution treated with 3% Ca(OH)$_2$ | 80.8 | 20.1 | 11.6 | 208.0 (alkalinity) | 2148 | n.a. | 97.13 | — |
| Initial solution | 79.5 | 20.4 | 5.1 | 180.0 (acidity) | 2907 | n.a. | 96.32 | — |
| Solution treated with 3.5% Ca(OH)$_2$ | 78.9 | 20.6 | 10.7 | 66.2 (alkalinity) | 3033 | n.a. | 98.24 | — |

It is noted from the data presented in the table that, also with use of solutions of crude caprolactam with great variability and relatively low degree of purity, as shown in particular by the indicator "acidity", the treatment according to the present invention makes it possible to obtain a neutralizing effect and a significant improvement of the purity measured by way of gas chromatography.

The solid discharged from the filtration during the course of these tests had, on average, the following composition range:

Total dry material: 70-80%
Humidity: 30-20%

On the basis of the total humid mass, the ashes accounted for approximately 30-35%, of which 35-45% was formed by organic substances. Caprolactam was revealed to be present in very modest levels (equal to a few percentage points), which signifies a considerable removal of the organic impurities, even if these were present in elevated amounts in the starting solution of crude caprolactam.

Example 7

Treatment with Ca(OH)$_2$

The following were introduced into the same reactor for Example 1 under application of the same process parameters:

solution of crude caprolactam with 72-73% of caprolactam from a HAS Raschig process: 45.00 kg;

30% by weight anhydrous solid Ca(OH)$_2$ dispersion in demineralized water maintained under stirring: 3.85 kg (1.15 kg dry).

In this case the Ca(OH)$_2$ was mixed with the solution of crude caprolactam in the form of a 30% by weight slurry pre-dispersed in demineralized water, keeping the stirring constant.

The concentration of the hydroxide is thus equivalent to 2.5% by weight of the solution of crude caprolactam. The temperature of the hot stage was 85° C.

The analytical data of the initial, untreated solution and of the treated solution are as follows:

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Initial solution | 72.1 | 28.0 | 5.9 | 9.4 (acidity) | 1185 | 0.0 | 99.7 | 9 + 1 (CPL) |
| Treated solution | 69.9 | 29.8 | 11.2 | 58.7 (alkalinity) | 1450 | 0.21 | 99.9 | 3 + 1 (CPL) |

It is noted that the pre-dispersion of Ca(OH)$_2$ in demineralized water leads to the same results obtained with the direct addition of solid Ca(OH)$_2$ in the solution of crude caprolactam.

Example 8

Treatment with Mg(OH)$_2$

The following were introduced into the same reactor for Example 1 under application of the same process parameters:

solution of crude caprolactam with 72-73% of caprolactam from a recovery process: 45.00 kg;

anhydrous solid $Mg(OH)_2$: 1.15 kg.

The concentration of the hydroxide is thus equivalent to 2.5% by weight. The temperature of the hot stage was maintained at 85° C.

The analytical data of the initial, untreated solution and of the treated solution are as follows:

| Sample | CPL refract [%] | H₂O KF [%] | pH | Acidity or alkalinity [meq/kg] | Consumption of KMnO₄ [mg/kg solut.] | Ashes [%] | GC purity CPL [% area] | GC n° peaks |
|---|---|---|---|---|---|---|---|---|
| Initial solution | 82.0 | 17.4 | 4.4 | 133.40 (acidity) | n.a. | 0.12 | 95.60 | 22 + 1 (CPL) |
| Treated solution | 83.1 (evap) | 17.1 | 6.7 | 49.7 (alkalinity) | n.a. | 0.29 | 97.34 | 11 + 1 (CPL) |

Magnesium hydroxide has effects similar to those of calcium hydroxide.

Example 9

Treatment with CaO

The following were introduced into the same reactor for Example 1 under application of the same process parameters:

solution of crude caprolactam with 72-73% by weight of caprolactam from a Raschig process: 45.00 kg;

anhydrous solid CaO: 0.90 kg.

Calcium oxide, in contact with water, transforms almost immediately into hydroxide, with production of heat, according to the following reaction:

By using calcium oxide (or magnesium oxide) in aqueous pre-dispersion, or by subsequent contact of the oxide with the water of the solution of crude caprolactam, the effective compound that reacts is therefore still the hydroxide.

The operating temperature was held at 85° C. The concentration of the oxide is equivalent to 1.95% by weight, but for the above-cited reaction it is equivalent to the concentration of 2.5% by weight of calcium hydroxide.

The analytical data of the initial, untreated solution and of the treated solution are as follows:

It is noted that, also with the use of calcium oxide, effects equivalent to those obtained with the use of calcium hydroxide are obtained, with the same starting material and conditions.

Example 10

Treatment with $Al(OH)_3$

Aluminum hydroxide ($Al(OH)_3$) is obtained by hydrating aluminum oxide. Aluminum is not part of the family of alkaline earth metals and is trivalent, whereas the alkaline earth metals used in this process are bivalent. However, aluminum demonstrates behaviors highly similar to the alkaline earth metals, and aluminum hydroxide is widely available at very modest cost.

The following were introduced into the same reactor for Example 1 under application of the same conditions:

solution of crude caprolactam with 73-75% by weight of caprolactam from a recovery process: 45.00 kg;

anhydrous solid $Al(OH)_3$: 0.45 kg-1.35 kg.

The concentration of the hydroxide is equivalent to 1.0% and to 3.0% by weight, respectively. The temperature of the hot stage was held at 75° C., whereas it was held at 25-35° C. during the course of the subsequent cooling. For aluminum hydroxide as well, the contact times for both stages of treatment were maintained at the levels indicated in the examples above.

The analytical data of the initial, untreated solution and of the treated solution are as follows:

| Sample | CPL refract [%] | H₂O KF [%] | pH | Acidity or alkalinity [meq/kg] | Consumption of KMnO₄ [mg/kg solut.] | Ashes [%] | GC purity CPL [% area] | GC n° peaks |
|---|---|---|---|---|---|---|---|---|
| Initial solution | 72.1 | 28.0 | 5.9 | 9.4 (acidity) | 1185 | 0.0 | 99.7 | 9 + 1 (CPL) |
| Solution treated at 85° C. | 78.3 (evap) | 21.8 | 11.2 | 73.4 (alkalinity) | 1073 | 0.31 | 99.9 | 4 + 1 (CPL) |

| Sample | CPL refract [%] | $H_2O$ KF [%] | pH | Acidity or alkalinity [meq/kg] | Consumption of $KMnO_4$ [mg/kg solut.] | Ashes [%] | GC purity CPL [% area] | GC n° peaks |
|---|---|---|---|---|---|---|---|---|
| Initial solution | 72.41 | 27.6 | 5.01 | 38.14 (acidity) | n.a. | n.a. | 97.93 | 18 + 1 (CPL) |
| Solution treated with 1.0% of $Al(OH)_3$ | 81.9 (evap) | 18.8 | 10.2 | 24.4 (alkalinity) | n.a. | 0.19 | 98.48 | 14 + 1 (CPL) |
| Solution treated with 3.0% of $Al(OH)_3$ | 80.7 (evap) | 19.1 | 11.4 | 36.4 (alkalinity) | n.a. | 0.45 | 99.29 | 11 + 1 (CPL) |

It is noted that, also with the use of aluminum hydroxide, both a reduction of the number of byproducts and a reduction of the amount of some byproducts compared to the initial level are observed.

Example 11

Treatment with $Ca(OH)_2$ and Final Purification of Caprolactam

A solution of crude caprolactam was treated with $Ca(OH)_2$ in the same reactor for Example 2 and under application of the same conditions. The solution of crude caprolactam used was derived from a traditional process, in which a reaction is performed between cyclohexanone and hydroxylamine sulfate in order to produce the cyclohexanone oxime, followed by a Beckmann rearrangement and separation of the ammonium sulfate. The treatment was performed using a temperature of 85° C. in the hot stage and two concentrations of $Ca(OH)_2$: 3.0% by weight in the first case and 3.5% by weight in the second case. The treated solution, after filtration, had the following characteristics:

| Sample | CPL refract [%] | $H_2O$ KF [%] | pH | Acidity or alkalinity [meq/kg] | Consumption of $KMnO_4$ [mg/kg solut.] | Ashes [%] | GC purity CPL [% area] | GC n° peaks |
|---|---|---|---|---|---|---|---|---|
| Solution treated with 3.0% of $Ca(OH)_2$ | 73.0 | 26.80 | 10.8 | 83.4 (alkalinity) | 1580 | 0.41 | 98.48 | 14 + 1 (CPL) |
| Solution treated with 3.5% of $Ca(OH)_2$ | 72.9 | 26.75 | 11.9 | 95.6 (alkalinity) | 1200 | 0.45 | 99.29 | 11 + 1 (CPL) |

The two samples of treated solution were then subjected to a final purification according to the present invention: firstly, a dehydration was performed in order to remove the water, followed by evaporation of the caprolactam in order to separate the salts of the alkaline compounds of polyvalent metals and by rectification of the caprolactam in order to separate the light byproducts and heavy byproducts.

The final purification of the two solution samples was performed in a batch-type facility equipped with two columns: the first was used for complete dehydration of the samples, and the second (equipped with structured packages of the Sulzer BX type) was used to perform, in succession, the phases of evaporation of caprolactam in order to separate the salts of the alkaline compounds of polyvalent metals and of rectification in order to separate the light byproducts and the heavy byproducts. In particular, the characteristics of the final purification process performed for these samples were as follows:

evaporation of water under moderate vacuum and at temperatures below 100° C. by means of the smaller column; final water evaporation parameters: pressure equal to 120 mbar; temperature between 48° C. and 50° C.;

evaporation and rectification (by means of the larger column equipped with Sulzer structured packages) of the fractions of caprolactam obtained under high vacuum in multiple steps; the temperature at the top of the column was between 122° C. and 127° C. and the pressure was equal to approximately 6 mbar.

The facility was fed with approximately 45-55 kg of solution; the removal of water and the fractionation of the caprolactam required the same time of two days each.

The results of the main quality parameters of the central fraction, equivalent to those of the final yield of rectified caprolactam following treatment with 3.0% and 3.5% of $Ca(OH)_2$ as described above are presented below, compared with the standard specification of commercial caprolactam.

| Sample | Volatile bases [meq/kg] | Permanganate index (IP) | Permanganate number [dry] [PN] | Absorbance at 290 nm | APHA | pH | Acidity [meq/kg] | Alkalinity [meq/kg] |
|---|---|---|---|---|---|---|---|---|
| Standard | <0.5 | <5 | >15000 | <0.05 | <5 | n.a. | <0.05 | <0.1 |
| Solution treated with 3.0% Ca(OH)$_2$ | 0.35 | 3.6 | 15512 | 0.043 | 2.96 | 6.9 | 0.01 | — |
| Solution treated with 3.5% Ca(OH)$_2$ | 0.45 | 2.94 | 15138.8 | 0.04 | 1.93 | 7.5 | — | 0.05 |

The analytical methods used to verify the quality parameters are those standardized and commonly used for caprolactam.

Example 12

Treatment with Ca(OH)$_2$ and Final Purification of Caprolactam Using Traces of Sodium Hydroxide in Rectifications Steps A solution of crude caprolactam was treated with Ca(OH)$_2$ in the same reactor for Example 2 and under application of the same conditions. The solution of crude caprolactam used was derived from a traditional process through Beckmann rearrangement after separation of the ammonium sulfate. The treatment was performed using a temperature of 85° C. in the hot stage and the concentration of Ca(OH)$_2$: 2.5% by weight. The treated solution, after filtration, had the following characteristics:

rectification. In both cases the final purification was performed in a batch-type facility equipped with two columns: the first was used for complete dehydration of the samples, and the second (equipped with structured packages of the Sulzer BX type) was used to perform, in succession, the phase of evaporation of caprolactam in order to separate the salts of the alkaline compounds of polyvalent metals.

The following conditions were used in the first step:

evaporation of water under moderate vacuum and at temperatures below 100° C. by means of the smaller column; final water evaporation parameters: pressure equal to 120 mbar; temperature between 48° C. and 50° C.;

evaporation of the raw caprolactam under high vacuum with the temperature at the top of the column between 122° C. and 127° C. and pressure equal to approximately 6 mbar.

The raw evaporated caprolactam obtained from this first step was used to perform two final rectifications in order to separate the light byproducts and the heavy byproducts without and with some Sodium Hydroxide contact.

| Sample | CPL refract [%] | H$_2$O KF [%] | pH | Acidity or alkalinity [meq/kg] | Consumption of KMnO$_4$ [mg/kg solut.] | Ashes [%] | GC purity CPL [% area] | GC n° peaks |
|---|---|---|---|---|---|---|---|---|
| Solution treated with 2.5% of Ca(OH)$_2$ | 70.33 | 31.0 | 11.43 | 133.4 (alkalinity) | 1025 | 0.21 | 99.68 | 7 + 1 (CPL) |

The sample of treated solution were then subjected to a final purification according to the present invention: firstly, a dehydration was performed in order to remove the water, followed by evaporation of the caprolactam in order to separate the remaining soluble organic salts of the alkaline compounds of polyvalent metals and then the collected raw evaporated caprolactam was divided in two parts:

1°-First part was sent to final rectification as it was;
2°-Second part of raw evaporated caprolactam was first melted (REMARK: FOR THIS TRIAL THE PRODUCT WAS RECOVERED AND REMELTED, WHILE IN THE CONTINOUS PROCESS THE CAPROLACTAM IS ALWAYS MANTAINED IN MOLTEN SATE) and mixed with 0.2% of NaOH and was left in contact for 2 hours at 90° C. under nitrogen and then sent to final The usual parameters conditions for caprolactam distillation were adopted:

rectification (by means of the larger column equipped with Sulzer structured packages) of the fractions of caprolactam at the temperature on the top of the column maintained between 122° C. and 127° C. and the pressure equal to approximately 6 mbar.

The parameters for distillation were the same for both cases.

The results of the main quality parameters of the central fraction, equivalent to those of the final yield of rectified caprolactam, without and with presence of the NaOH are presented below compared with the standard specification of commercial caprolactam.

| Sample | Volatile bases [meq/kg] | Permanganate index (IP) | Permanganate number [dry] [PN] | Absorbance at 290 nm | APHA | pH | Acidity [meq/kg] | Alkalinity [meq/kg] |
|---|---|---|---|---|---|---|---|---|
| Standard | <0.5 | <5 | >15000 | <0.05 | <5 | n.a. | <0.05 | <0.1 |
| Solution treated with 2.5% Ca(OH)$_2$ No NaOH | 0.45 | 5.5 | 5300 | 0.055 | 1.51 | 6.9 | 0.01 | — |
| Solution treated with 2.5% Ca(OH)$_2$ With NaOH | 0.27 | 1.3 | 19100 | 0.034 | 1.93 | 7.4 | — | 0.045 |

The final rectification using some trace of NaOH in anhydrous condition in contact with the caprolactam remain one additional method to improve the final quality of the product also in combination with the polyvalent metals alkaline treatment.

The analytical methods used to verify the quality parameters are those standardized and commonly used for caprolactam.

The invention claimed is:

1. A process for the purification of caprolactam from a solution of crude caprolactam, characterized in that said process comprises the following steps:
   (i) treating the solution of crude caprolactam by means of direct contact with one or more alkaline compounds of polyvalent metals, at a temperature between 50° C. and 110° C., for a duration from 1 hour to 5 hours, under stirring, so as to thus obtain a suspension, wherein said one or more alkaline compounds of polyvalent metals are selected from the group formed of: bivalent alkaline earth metal hydroxides, bivalent alkaline earth metal oxides, amphoteric polyvalent metal hydroxides having alkaline behavior when placed in contact with acids, amphoteric polyvalent metal oxides having alkaline behavior when placed in contact with acids and mixtures thereof;
   (ii) cooling the suspension of step (i) and holding it at a temperature between 20° C. and 35° C., for a duration between 1 hour and 6 hours, under stirring;
   (iii) separating the solids from the suspension of step (ii) to obtain an aqueous solution of crude caprolactam.

2. The process according to claim 1, wherein said one or more alkaline compounds of polyvalent metals are present overall in an amount between 0.5% and 5% by weight relative to the total weight of the suspension.

3. The process according to claim 1, wherein said polyvalent metal is an alkaline earth metal selected from the group formed of calcium and magnesium.

4. The process according to claim 1, wherein the alkaline compound is aluminum hydroxide.

5. The process according to claim 1, wherein said one or more alkaline compounds of polyvalent metals is/are present overall in an amount between 2.0% and 3.5% by weight relative to the total weight of the suspension and in the form of an aqueous dispersion comprising 30-40% by weight of said alkaline compounds relative to the total weight of the aqueous dispersion.

6. The process according to claim 1, wherein the temperature in step (i) is between 80° C. and 95° C.

7. The process according to claim 1, wherein the duration of step (i) is between 2 hours and 3 hours.

8. The process according to claim 1, wherein the temperature in step (ii) is between 25° C. and 30° C.

9. The process according to claim 1, wherein the duration of step (ii) is between 2 hours and 30 minutes and 3 hours and 30 minutes.

10. The process according to claim 1, wherein the separation of the solids in step (iii) is performed in two steps, whereby in the first step the separation of most of the suspended solids is performed by centrifugation, and in the second step the filtration of the residual fine solids is performed by means of pressurized equipment equipped with filter cloths, whereby a layer of diatomaceous earth is applied to the filter cloths.

11. The process according to claim 1, wherein the solution of crude caprolactam is obtained by a process of caprolactam synthesis by way of Beckmann rearrangement of cyclohexanone oxime, or by a process for the recovery of caprolactam.

12. The process according to claim 1, further comprising, at the end of step (iii), the following steps:
   (iv) dehydrating the aqueous solution of caprolactam obtained in step (iii), at a temperature below 100° C. and at a pressure between 35 mbar and 45 mbar, thus obtaining an anhydrous crude caprolactam;
   (v) collecting and maintaining the anhydrous crude caprolactam at 110-120° C. under inert atmosphere of nitrogen for 1.5-2.5 hours in a stirred reactor to complete the transformation of the residual organic salts;
   (vi) evaporating the crude anhydrous caprolactam obtained in step (v), thus separating the salified polyvalent alkaline compounds;
   (vii) rectifying the caprolactam obtained in step (vi) by means of a vacuum fractional distillation column equipped with structuring packages, separating and purging the light byproducts;
   (viii) rectifying the caprolactam obtained in step (vii) by means of a vacuum fractional distillation column equipped with structured packages, separating the purified caprolactam from the heavy byproducts;
   (ix) squeezing the product remaining at the bottom of the column at the end of step (viii) and rectifying the caprolactam thus obtained by means of a vacuum fractional distillation column, equipped with structured packages, thus recovering a further amount of residual caprolactam.

13. The process according to claim 12, further comprising a squeezing of caprolactam from the residual materials obtained from step (vi) of evaporation, and rectifying the liquid component thus obtained by way of a vacuum fractional distillation column, equipped with structured packages, thus recovering a further amount of residual caprolactam.

14. The process according to claim 12 wherein the dehydrated anhydrous caprolactam from step (vi) is mixed with traces of NaOH in the amount from 0.05-0.5 by weight relative to anhydrous caprolactam, and said mixture is then submitted to the rectification/distillation steps.

* * * * *